United States Patent [19]
Rhyne

[11] Patent Number: 5,083,018
[45] Date of Patent: Jan. 21, 1992

[54] FLUID INDEX OF REFRACTION SENSOR

[75] Inventor: George W. Rhyne, Mesa, Ariz.

[73] Assignee: Motorola, Inc., Schaumburg, Ill.

[21] Appl. No.: 550,934

[22] Filed: Jul. 11, 1990

[51] Int. Cl.$^5$ .............................................. H01J 5/16
[52] U.S. Cl. .................. 250/227.25; 356/133
[58] Field of Search ............... 250/227.25, 577, 574; 356/133, 135, 136, 137

[56] References Cited

U.S. PATENT DOCUMENTS

| | | | |
|---|---|---|---|
| 4,672,196 | 6/1987 | Canino | 250/225 |
| 4,824,244 | 4/1989 | Miyata et al. | 356/128 |
| 4,895,444 | 1/1990 | Miyata et al. | 356/133 |

*Primary Examiner*—David C. Nelms
*Assistant Examiner*—T. Davenport
*Attorney, Agent, or Firm*—Stuart T. Langley

[57] ABSTRACT

An index of refraction sensor having a photo detector array with variable sized elements is provided. The photo diode array comprises a plurality of diodes with varying area. The diodes farthest from a light emitting diode having a larger area than those closer to the light emitting diode. Preferably the diode area is designed so that each of the diodes produces approximately the same current output when exposed to light from the LED. Each diode in the photo diode array is sequentially powered and the photo diode outputs are summed together. A power input from a first diode in the array is coupled to a start input of a time measurement circuit. The summed output of the photo diode array is coupled to a stop input of the time measurement circuit. Elapsed time measured by the time measurement circuit is thus a function of reflected light edge location, and therefore a function of index of refraction of the fuel mixture.

12 Claims, 2 Drawing Sheets

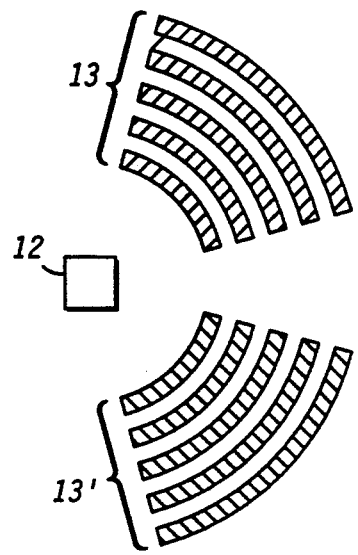
*FIG. 3*
*FIG. 4*
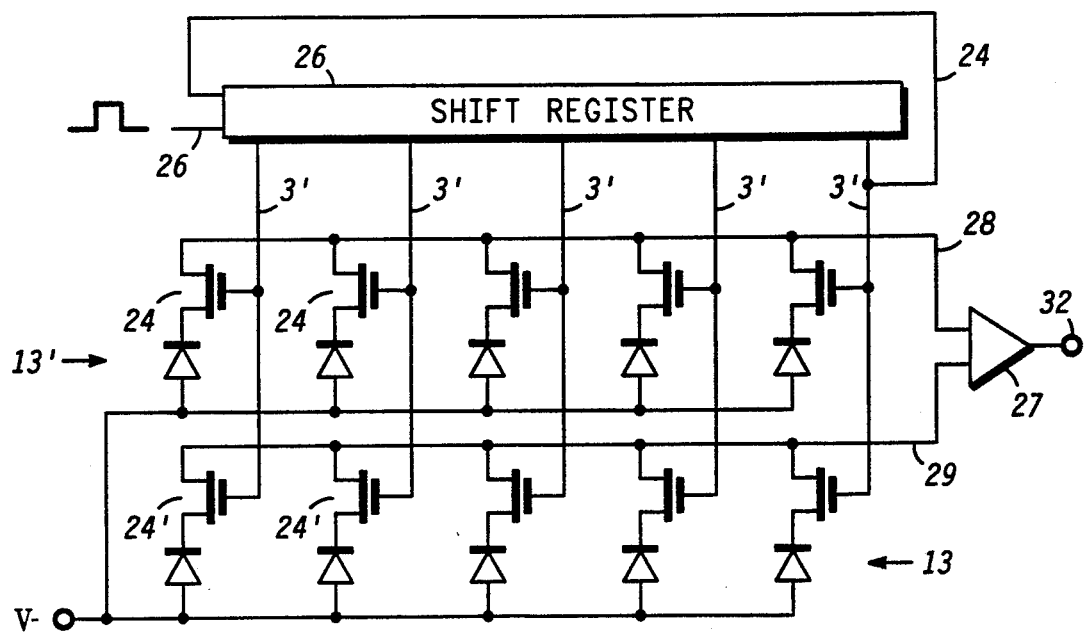

FLUID INDEX OF REFRACTION SENSOR

BACKGROUND OF THE INVENTION

This invention relates, in general, to a fluid index of refraction sensor, and more particularly, to a sensor for measuring index of refraction of a liquid fuel.

It is becoming increasingly common to use liquid fuel mixtures such as gasoline/alcohol and gasoline/ether for automobiles. This is particularly true in congested urban areas where the use of gasoline mixtures reduces pollutant emissions. Further, gasoline is a non-renewable resource while alcohol and other gasoline substitutes are renewable. Thus, it is expected that the use of liquid fuel mixtures and alternative fuels will increase dramatically in coming years. To provide maximum utility, automobile engines must be able to run on a variety of fuels and fuel mixtures.

One problem encountered in using alternative fuels and fuel mixtures is that to achieve optimum fuel efficiency and minimum pollutants it is necessary to adjust spark timing and fuel-air mixture being delivered to a cylinder depending upon the ratio of alcohol in the alcohol/gasoline mixture. This is particularly true as the percentage of alcohol increases and when pure alcohol is used. To use alternative fuels effectively an engine must be able to re-tune itself each time the fuel mixture changes. Thus, it is important to monitor the fuel mixture constantly so that the fuel-air mixture and spark timing can be adjusted when a new fuel source is used. Further, it is useful if this monitoring can be done electronically so that the data can be easily used by on board computers and electronic fuel injection systems.

It is known that the index of refraction for gasoline changes substantially when alcohol or other gasoline substitutes are added to the gasoline. Is also known that index of refraction of a fluid can be determined by measurement of a critical angle of light reflection from the fluid. Sensors are available which use this critical angle change to indicate the amount of alcohol which is in the gasoline/alcohol mixture. One such sensor is described in U.S. Pat. No. 4,895,444 issued to Miyata et al. This fuel sensor used a transparent window having a light emitting diode and a single light detector mounted underneath the window. The outer surface of the transparent window was exposed to the fuel mixture. Provided that the index of refraction of the window ($n_w$) was greater than that of the fluid ($n_f$), all rays of incident light with incidence angles greater than the critical angle will be reflected towards the detector. Thus, depending on the geometry of the sensor and the index of refraction of the fluid, a variable amount of the detector would be exposed to light, generating a signal with an amplitude which was a function of the index of refraction of the fluid. This signal was not, however, a linear function of index of refraction, and was temperature dependent and subject to distortion in a noisy automotive environment.

It would be desirable to have an index of refraction sensor that is not temperature sensitive and provides greater sensitivity and precision. Improved temperature sensitivity and precision has been achieved using a linear detector array rather than a single light detector element. Such a sensor is described in co-pending U.S. Pat. application Ser. No. 491,772 assigned to the same assignee as the present invention. The detector array could be scanned using a simple shift register circuit to produce an output waveform having a pulse width which was proportional to index of refraction of the gasoline/alcohol mixture. Although this method improved precision and accuracy, the detector array produced a relatively low amplitude signal which complicated signal processing in a noisy automotive environment. Also, the linear photo detector array resulted in an unbalanced detector output since the detector elements farthest from the LED source produced a much lower amplitude output than those elements nearest the LED source. It has been found that current amplitude from the linear detector can vary by a factor of more than 300% across the detector.

Accordingly, it is an object of the present invention to provide an index of refraction sensor with improved signal amplitude.

Another object of the present invention is to provide an index of refraction sensor using an arc-shaped photo diode array.

Another object of the present invention is to provide an index of refraction sensor with a photo detector array having a balanced output from each element of the array.

A further object of the present invention to provide an index of refraction sensor having a photo detector array wherein the size of each element of the array is non-uniform.

SUMMARY OF THE INVENTION

These and other objects and advantages of the present invention are achieved by an index of refraction sensor having a photo detector array with variable sized elements. A light emitting diode and a photo diode array are mounted on a second surface of a window which is exposed to a fuel mixture. Light traveling from the light emitting diode is incident upon an interface of the window and the fuel mixture and a portion of the incident light reflects from the interface towards the photo diode array. A critical angle at which incident light will reflect is determined by the index of refraction of the fuel mixture.

The photo diode array comprises a plurality of diodes with varying area. The diodes farthest from the light emitting diode have a larger area than those closer to the light emitting diode. Preferably the diode area is designed so that each of the diodes produces approximately the same current output when exposed to light from the LED. Each diode in the photo diode array is sequentially powered and the photo diode outputs are summed together. A power input from a first diode in the array is coupled to a start input of a time measurement circuit. The summed output of the photo diode array is coupled to a stop input of the time measurement circuit Elapsed time measured by the time measurement circuit is thus a function of reflected light edge location, and therefore a function of index of refraction of the fuel mixture.

BRIEF DESCRIPTION OF THE DRAWINGS

FIG. 3 illustrates a plan view of a second embodiment of the present invention; and FIG. 4 illustrates a schematic diagram of a circuit used to process output from the sensor shown in FIG. 3.

DETAILED DESCRIPTION OF THE DRAWINGS

Figure 1:
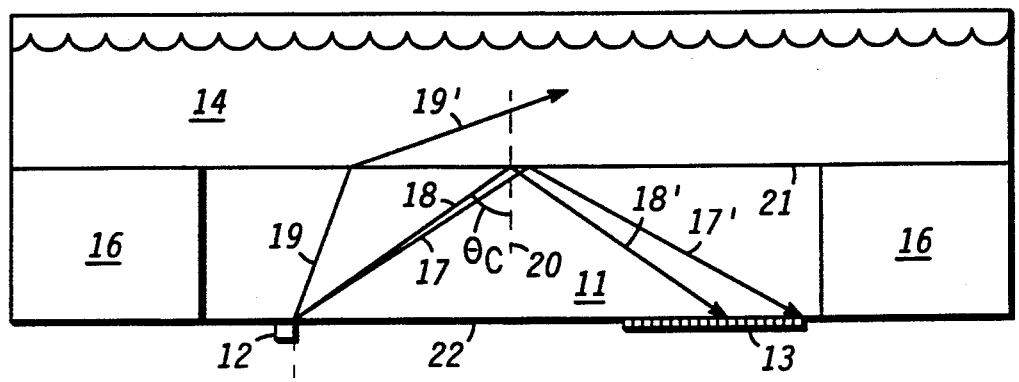
FIG. 1 illustrates a cross-sectional view of an index of refraction sensor of the present invention.

FIG. 1 illustrates a cross-sectional view of the index of refraction sensor 10 of the present invention. Sensor 10 comprises transparent block or window 11 having a first surface 21 and a second surface 22 with a light emitting diode (LED) 12 and a light detector 13 mounted on second surface 22. Preferably, sides of window 11 are coated with the light absorbing material 16 to reduce undesirable internal reflections. It may also be desirable to coat portions of surface 21 with a light absorbing material to reduce undesirable internal reflections and to ensure that stray light does not enter window 11 through surface 21. It should be understood that LED 12 is intended to encompass any approximate point source of electromagnetic radiation, and may emit wavelengths outside of the visible spectrum. Light detector 13 may comprise a photo diode array, a charge coupled device (CCD), or the like.

As will be apparent to those of skill in the art, light emitting diode 12, detector 13, and window 11 could be manufactured on a single semiconductor substrate such as gallium arsenide. Further, these devices as well as light absorbing material 16 could be fabricated using conventional semiconductor processing techniques. However, in view of current costs for gallium arsenide substrates, it is believed that it is more cost effective to manufacture the index of refraction sensor 10 of the present invention with discrete components mounted to window 11. Also, by using discrete components LED 12 and detector 13 are not exposed to a harsh fuel environment. Alternatively, detector 13 can be integrated with detector electronics, to be described hereinafter, on a single silicon substrate and used with a discrete LED 12.

Fluid 14 is placed in contact with surface 21 of window 11. Light emitting diode 12 emits light of substantially equal intensity in all directions through window 11. Because LED 12 and detector 13 are both mounted on surface 22, the only light which reaches detector 13 must reflect from surface 21. When an opaque material 16 is used on the sidewalls of window 11 internal reflection of light from LED 12 is greatly reduced thereby improving the signal-to-noise ratio of a signal generated by detector 13.

In operation, light beams 17, 18, and 19, which are emitted from LED 12, travel towards surface 21. Although only three light beams are shown in the Figure, it should be understood that an infinite number of beams are produced by LED 12. Fluid 14 has an index of refraction $n_f$ and window 11 has an index of refraction $n_w$. As long as $n_w > n_f$ some light will reflect from surface 21, which is an interface between fluid 14 and window 11. There exists a critical angle ($\theta_c$) for total internal reflection which is a function of index of refraction of window 11 ($n_w$) and the index of refraction of fluid 14 ($n_f$). $\theta_c$ is measured from line 20 which is normal to surface 21, and illustrated in the figure by a dashed line. As illustrated, beam 19 has the lowest angle of incidence and beam 17 the highest angle of incidence. Light beams emitted from LED 12 having an angle of incidence less than the critical angle will be refracted as indicated by light beam 19'. Thus refracted beam 19' will pass through surface 21 into fluid 14. Light beams 17 and 18 which have an angle of incidence greater than the critical angle are totally reflected by surface 21 thereby producing reflected beams 17' and 18' which fall on detector 13.

In a preferred embodiment, window 21 comprises a material having an index of refraction $n_w$ of approximately 1.91 and is approximately 3 millimeters thick. Fluid 14 comprises a gasoline-alcohol mixture having an index of refraction $n_f$ at room temperature ranging from 1.33 to 1.43, depending on the exact ratio of alcohol to gasoline. The critical angle ($\theta_c$) can be described by the equation:

$$\theta_c = \sin^{-1}\left(\frac{n_f}{n_w}\right)$$

or for the preferred embodiment described above $\theta_c$ is approximately 45 degrees. It should be noted that in the preferred embodiment $n_w$ was chosen to produce a $\theta_c$ of approximately 45 degrees. To achieve a different $\theta_c$ one needs merely to choose a window material with a different index of refraction.

As the fluid index of refraction $n_f$ changes, reflected light beams 17' and 18' will cover different portions of detector 13. Light emitting diode 12 must be separated from detector 13 by a predetermined distance so that light beams corresponding to critical angles of interest fall on detector 13. This critical distance ($D_{CR}$) can be found by the equation:

$$D_{CR} = 2 \cdot T_w \cdot \tan \theta_c,$$

where $T_w$ is the thickness of window 11. The following table summarizes the change in critical angle and critical distance for typical values of $n_f$ for gasoline-alcohol mixtures:

| $n_f$ | $\theta_c$ | $D_{CR(mm)}$ |
|---|---|---|
| 1.34 | 44.6 | 5.9 |
| 1.35 | 45.0 | 6.0 |
| 1.36 | 45.4 | 6.1 |

In the example given above where $T_w$ equals 3 mm, it can be seen that the critical distance will move in a range of nearly 180 microns as the fluid index of refraction changes.

When $n_f$ is such that $\theta_c = 44.6°$, light rays 17 and 18 will reflect and reach detector 13. When $n_f$ is such that $\theta_c = 45.4°$, however, only light beam 17 will reflect, while light beam 18 will refract into fluid 14. Thus, a larger area of detector 13 is exposed to light at lower critical angles.

Preferably, detector 13 comprises a photo diode array in which case only diodes in the array which are exposed to light will produce the signal and the remaining diodes will produce no signal at all. A photo diode array will produce a differential output rather than the analog signal of a single diode detector. The use of a photo diode array for detector 13 has the advantage of more accurately detecting the actual critical distance, and thus the actual critical angle. Using a photo diode array, the critical angle is detected by the number of diodes in the array which are activated, and not the magnitude of the light striking the array. The differential output of a photo diode array is highly insensitive to temperature changes in LED 12 and detector 13. A charge coupled device may also be used for detector 13 to produce a differential output.

It should be noted that reflected beam 17' travels significantly farther in window 11 than does beam 18'.

Normal attenuation and beam spreading in window 11 causes amplitude of beam 17' to be much lower than that of beam 18' when the beams reach detector 13. This results in a lower amplitude signal from elements of detector 13 which are farther from LED 12, or in other words an unbalanced output. This effect is complicated when LED 12 has a nonuniform radiation pattern such that incident beam 17 has a lower amplitude than beam 18 from the moment it is emitted, as is common in LED's.

Figure 2:
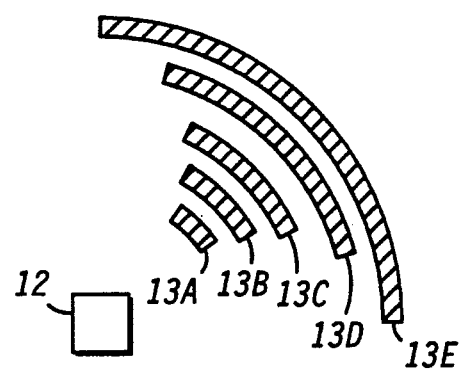
FIG. 2 illustrates a plan view of a first embodiment of the sensor shown in FIG. 1.

It has been found that these effects can be compensated by using a detector array 13 wherein each element has a different area as shown in FIG. 2. Detector 13 shown in FIG. 1 comprises arc shaped detector elements 13A-13E concentrically aligned around LED 12. Output amplitude of each element 13A-13E is a function of length of that element. Elements 13E, which are farthest from LED 12, have a larger area than elements 13A, which are closer. When elements 13A-13E subtend the same angle, the elements farthest, i.e. 13E, from LED 12 will have a larger area, and therefore a larger output current, than those elements, i.e. 13A, closer to LED 12.

Each element 13A-13E is preferably sized to provide a similar current output when illuminated, resulting in a balanced output of detector 13. To balance the output it is recommended that each segment 13A-13E subtend a different angle, hereinafter referred to as a non-uniform detector array. For example, element 13E is illustrated subtending an angle of 90°, while element 13D is shown subtending approximately a 60° arc length. A feature of the non-uniform detector array is that resolution of the sensor can be determined independent of output signal amplitude. Resolution of the array is determined by width of each element indicated by arrows W in FIG. 2. The sensor is designed by fixing element width to provide desired resolution, then adjusting element lengths to provide the necessary output level. To provide a balanced output, each element should have a greater arc length than the preceding element.

Another embodiment of the sensor of the present invention is shown in FIG. 3. FIG. 3 shows each element in detectors 13 and 13' having the same arc length. Although each segment is illustrated as subtending an angle of approximately 60°, it should be understood that any angle may be used. Also, variable angles as shown in FIG. 2 may be used to achieve more balanced output. The uniform arc length shown in FIG. 3 may be suitable for some applications even though it does not provide the most balanced output which is possible.

The embodiment in FIG. 3 is distinctive in that a dark detector array 13' is provided. Dark detector array 13' is geometrically a duplicate of detector array 13 and is placed very near detector array 13. As the name implies, dark detector 13 is shielded from any light emitted by LED 12 by an opaque mask (not shown) formed over the array. The output of dark array 13' is thus a function of background noise and temperature. Output from each element in dark array 13' can be subtracted from the output of a corresponding element in detector array 13 to improve signal to noise ratio of the sensor.

FIG. 4 illustrates a circuit useful in processing the output of the detector array shown in FIG. 3. Each element of detector array 13 is coupled through a switch 24 to a common output bus 28. Each element of dark detector array 13' is similarly coupled through a switch 24' to a second output bus 29. Switches 24 are controlled by output of shift register 26. Shift register 26 has a clock input 26 which is continuously pulsed to move data from input 24 sequentially to each output 31. Each output 31 is coupled to one switch 24 and one switch 24'. Only one output 31 is allowed to be active at any time. When any output 31 is active, one element of detector array 13 is coupled to bus 28 and a corresponding element of dark detector array 13 is coupled to bus 29. In this manner, arrays 13 and 13' are continuously scanned. Corresponding elements of detector array 13 and dark detector array 13' have similar area and are located near each other.

Output bus 28 and output bus 29 are coupled to transimpedance amplifier 27 which differentially amplifies a current signal on buses 28 and 29 and outputs a voltage signal on output 32. This output voltage signal is a series of pulses wherein each pulse amplitude is a function of light received on a particular element of detector array 13. The output signal can be monitored to determine which elements of array 13 are exposed to light, which in turn reveals index of refraction of fluid 14 shown in FIG. 1.

Alternatively, voltage across each element of detector 13 and dark detector 13' can be monitored, rather than the current. This can be accomplished by substituting a differential voltage amplifier for transimpedance amplifier 27 and providing additional scanning electronics to discharge each element of arrays 13 and 13' once it is sampled. A voltage signal is generated in each element of detectors 13 and 13' due to charge build up while the element is exposed to light from LED 12. Using the voltage signal, though increasing circuit complexity somewhat, should yield improved signal to noise ratio.

Output processing circuitry shown in FIG. 4 can be integrated monolithically with light detecting arrays 13 and 13' shown in FIG. 3. Although somewhat more complicated, LED 12 may also be integrated monolithically with the other components. For reasons set out earlier, it may be more cost effective to use a separate device for light emitting diode 12, although monolithic integration is certainly possible.

Improved performance may be achieved by using locking signal processing techniques. Using this technique, LED 12 is pulsed briefly at a regular frequency. While LED 12 is on, detector 13 and dark array 13' are analyzed to detect index of refraction. While LED 12 is off, detector 13 and dark array 13' are analyzed to detect a background noise level. This technique allows LED 12 to be pulsed at higher power than a constant DC bias would allow, and further improves signal to noise ratio of the sensor. Other similar signal processing techniques are equally applicable to the present invention.

By now it should be apparent that a fluid index of refraction sensor with improved output amplitude and signal to noise ratio is provided. Detector array 13 comprising elements having variable detector area is placed in the path of the reflected light resulting in a balanced output from each element of the array. By using concentric arc shaped elements for the detector array greater design flexibility is achieved, allowing independent design for precision and output level of the sensor. Using a dark detector array which corresponds element for element to the light detector array, a noise component of the signal from the light detector array can be compensated, increasing signal to noise ratio.

I claim:

1. An index of refraction sensor comprising: a transparent block having upper and lower surfaces and an index of refraction $n_w$, wherein the upper surface is exposed to a material having an index of refraction $n_f$, wherein $n_f$ is less than $n_w$; a light emitting device mounted on the lower surface; and a first array of light detecting devices mounted on the lower surface parallel to the lower surface and spaced from the light emitting device by a predetermined separation, wherein light detecting devices nearest the light emitting device are smaller than light detecting devices farthest from the light emitting device.

2. The sensor of claim 1 wherein the light detecting devices are arc shaped and arranged concentrically around the light emitting device.

3. The sensor of claim 1 wherein the light emitting device comprises a light emitting diode and the light detecting device comprises a photo-diode array.

4. The sensor of claim 1 wherein the light detecting array and the light emitting device are formed monolithically on a semiconductor device.

5. An index of refraction sensor comprising: a transparent block having upper and lower surfaces and an index of refraction $n_w$, wherein the upper surface is exposed to a material having an index of refraction $n_f$, wherein $n_f$ is less than $n_w$; a light emitting device mounted on the lower surface; and a first array of light detecting devices mounted on the lower surface and spaced from the light emitting device by a predetermined separation, wherein light detecting devices nearest the light emitting device are smaller than light detecting devices farthest from the light emitting device; and a second detector array comprising a plurality of elements which correspond to elements in the first detector array and an opaque coating shading the second detector array.

6. An index of refraction sensor comprising: a transparent block having upper and lower surfaces and an index of refraction $n_w$, wherein the upper surface is exposed to a material having an index of refraction $n_f$, wherein $n_f$ is less than $n_w$; a light emitting device mounted on the lower surface; and a first concentric array of arc shaped light detecting devices mounted on the lower surface and spaced from the light emitting device by a predetermined separation, wherein the light emitting device is at the center of the concentric array.

7. The sensor of claim 6 wherein the light emitting device comprises a light emitting diode and the light detecting device comprises a photo-diode array.

8. The sensor of claim 6 wherein the light detecting array and the light emitting device are formed monolithically on a semiconductor device.

9. An index of refraction sensor comprising: a transparent block having upper and lower surfaces and an index of refraction $n_w$, wherein the upper surface is exposed to a material having an index of refraction $n_f$, wherein $n_f$ is less than $n_w$; a light emitting device mounted on the lower surface; and a first concentric array of arc shaped light detecting devices mounted on the lower surface and spaced from the light emitting device by a predetermined separation, wherein the light emitting device is at the center of the concentric array; and a second detector array comprising a plurality of elements which correspond to elements in the first detector array and an opaque coating shading the second detector array.

10. The sensor of claim 9 further comprising a first means for scanning corresponding elements of the first and second detector arrays to sequentially couple each element of the first detector array to one input of a differential amplifier and each corresponding element of the second detector array to a second input of the differential amplifier.

11. The sensor of claim 9 wherein the differential amplifier comprises a transimpedance amplifier.

12. The sensor of claim 9 wherein the differential amplifier comprises a voltage amplifier and the sensor further comprises a second means for scanning which discharges the corresponding elements of the first and second detector arrays at a predetermined time after the corresponding elements have been coupled to the differential amplifier.

* * * * *